United States Patent [19]
O'Donnell, Jr.

[11] Patent Number: 6,142,989
[45] Date of Patent: Nov. 7, 2000

[54] APPARATUS AND METHOD FOR CUSTOMIZED LASER CORRECTION OF REFRACTIVE ERROR

[76] Inventor: Francis E. O'Donnell, Jr., 709 The Hamptons La., Town & Country, Mo. 63017

[21] Appl. No.: 08/771,802

[22] Filed: Dec. 20, 1996

Related U.S. Application Data

[63] Continuation-in-part of application No. 08/265,950, Jun. 27, 1994, abandoned, which is a continuation-in-part of application No. 08/055,862, May 3, 1993, abandoned, which is a continuation-in-part of application No. 08/055,578, May 3, 1993, abandoned.

[51] Int. Cl.$^7$ ..................................................... A61N 5/06
[52] U.S. Cl. ................................................. 606/5; 606/10
[58] Field of Search ....................................... 606/2, 3–19

[56] References Cited

U.S. PATENT DOCUMENTS

| | | | |
|---|---|---|---|
| 4,461,294 | 7/1984 | Baron | 606/5 |
| 4,669,466 | 6/1987 | L'Esperance | 606/11 |
| 5,152,759 | 10/1992 | Parel et al. | 606/5 |
| 5,188,631 | 2/1993 | L'Esperance, Jr. | 606/5 |

FOREIGN PATENT DOCUMENTS

| | | | |
|---|---|---|---|
| 9403133 | 2/1994 | WIPO | 606/4 |

*Primary Examiner*—David M. Shay
*Attorney, Agent, or Firm*—Paul M. Denk

[57] ABSTRACT

Improved methods of spherical and astigmatic laser correction. By using an array of micro-charge coupled devices, a spatially-resolved refractive error map is generated which guides the treatment process. Improved astigmatic correction is provided by avoiding laser treatment of the unaffected cornea. Complex astigmatic corrections including lenticular astigmatism and mixed astigmatism are treated by first sphericizing the corneal surface before correcting the residual refractive error.

8 Claims, 2 Drawing Sheets

APPARATUS AND METHOD FOR CUSTOMIZED LASER CORRECTION OF REFRACTIVE ERROR

CROSS-REFERENCE TO RELATED APPLICATION

This application is a continuation in part of the application having Ser. No. 08/265,950, filed Jun. 27, 1994, now abandoned, which was a continuation-in-part of the application having Ser. No. 08/055,862, filed on May 3, 1993 now abandoned, which was a continuation-in-part of the application having Ser. No. 08/055,578, filed on May 3, 1993 and entitled "Method of Calibrating Lasers for Use in Ophthalmological Surgery," now abondoned, all applications being owned by a common assignee.

BACKGROUND OF THE INVENTION

This invention involves a method and apparatus useful in doing ophthalmological surgery, more specifically, to an improved method of performing laser surgery to correct refractive error, including astigmatism.

Astigmatism is a visual impairment caused by a directional difference in refractive power of the cornea (and or lens) resulting in variations in refraction in the principal meridians of the eye. Prior art surgical techniques to correct the impairment consists of using laser such as a UV laser at 193 nm (excimer) or at 210 nm (diode-pumped fifth harmonic of a Nd:Yag) or an IR laser (erbium) at 2900 nm to ablate the corneal surface to correct the spherical portion of the refractive error as well as the cylindrical portion of the refractive error. The latter has been shaped by using an expanding slit, or a combination of slit and an iris diaphragm mask, to orient the ablation along the desired meridian of the cornea.

One variation of this technique is to use an erodible mask having the appropriate prescriptive power placed over the cornea to guide the surface ablation. One type of such erodible mask consists of a quartz blank with a polymethylmethacrylate (PMMA) lens (Summit Technologies Inc., Waltham, Mass.).

Alternatively, solid state lasers, such as the nano-second YAG and the holmium, are used to treat the corneal stroma in order to modify the surface curvature to correct the spherical and cylindrical refractive error of the eye.

There are notable deficiencies in the prior art techniques for correcting astigmatism with a surgical laser. One deficiency arises from the surgeon's dependence upon current refraction technologies. A second deficiency lies with surgical techniques that treat tissue in a manner resulting in an unwanted coupling effect, as will be further explained below.

Prior art techniques involve treating astigmatism by simply adding or subtracting astigmatism correction as determined by conventional refractive technology. In individual cases where refractive astigmatism is not the same as corneal astigmatism, conventional treatment can lead to an irregular corneal astigmatism due to the production of more than two principal meridians on the corneal surface.

As to the second major drawback to prior art astigmatism correction techniques, prior art interventions suffer from a lack of predictability and from the development of an unwanted coupling effect. Unwanted coupling effect results when the correction of the astigmatic error by surgical ablation creates an unwanted change in the corneal refractive power in the meridian 90° from the treated areas.

Moreover, in cases of compound hyperopic astigmatism and mixed astigmatism, prior art techniques of PRK fail to effectively neutralize the refractive error because of the complexity of the refractive solution. In compound hyperopic astigmatism, there are two focal points, both of which are located posterior to the retina. Prior art attempts to steepen differentially the two principle meridians have met with limited success because of coupling. In the case of mixed astigmatism, one focal point is in front of the retina and the other focal point is behind the retina. In this case, one principle meridian (the myopic focal point) must be flattened while the other principle meridian (the hyperopic focal point) must be steepened. Again, prior art techniques of differentially treating the two meridians have suffered from the adverse effects of coupling.

L'Esperance in U.S. Pat. No. 4,721,379, teaches the use of videokeratoscopic corneal topography data to guide the ablation process. L'Esperance incorrectly taught that corneal topography provides sufficient information to guide the ablation process. (In fact, Roberts has shown that videokeratoscopy provides curvature data but not true topography. True topography gives information about elevation and depression of a surface. True corneal topography alone still can not provide adequate information to guide the ablation process.) Although L'Esperance teaches the use of cornea thickness (pachymetry) as a useful adjunct to corneal topography, it has been determined that PRK (photorefractive keratectomy) does not depend upon corneal thickness since only superficial cornea is ablated.

The method of the present invention, however, solves, by vector analysis, the direction and magnitude of the underlying lenticular astigmatism. Thus identified, this invention eliminates any corneal astigmatism. The method then corrects the spherical refractive error and the lenticular astigmatic error. The advantage of this approach is that it reduces the risk of irregular astigmatism because only two principal meridians define the corneal refractive surface.

The present invention avoids the unwanted coupling effect by treating the responsible meridian in a graduated fashion and by sparing the center of the visual axis, i.e. the intersection of the line of sight with the cornea. It does this by using a pie-shaped treatment area with a gradual reduction in dioptric correction on either side of the mid-line of the segment. The present invention uses pie-shaped areas of ablation to achieve astigmatic correction. In contrast, Parel (U.S. Pat. No. 5,152,759) taught the use of arcuate shaped laser incision (cuts) to treat astigmatism, much like the arcuate incision made with knives for astigmatism treatment. In U.S. Pat. No. 5,188,636 L'Esperance taught the use of a transition zone at the junction between areas of ablation and nonablation (untreated) areas. In contrast, the present invention features a graded, stepwise ablation throughout the area of astigmatic treatment.

The present invention eliminates all corneal astigmatism by ablating the steepest meridian so that it has the same refractive power as the weaker meridian, thus "sphericizing" the cornea, and then it treats the resultant spherical hyperopia in compound hyperopia astigmatism and in mixed astigmatism.

In addition to improved astigmatic corrections, the present invention provides a method of improved laser correction of the spherical part of refractive error. Current refraction technologies measure only an average dioptric correction. That is, the normal cornea is aspheric and true refractive error is aspheric and varies across the entrance pupil. Basing laser correction on current refraction technologies results in a spherical correction for an aspheric refractive error. Prior art laser techniques rely on this refractive data alone to calculate the required spherical correction. The technique of the present invention uses a novel apparatus to measure point-to-point refractive data which is then used to guide the laser treatment to a full, customized correction of the individual refractive error.

The present invention teaches that point-to-point refractive error determination over the entrance pupil is a useful way to guide the PRK ablation. Real corneal topography information determined pre-operatively (not during the procedure as taught by L'Esperance) about corneal astigmatism is useful since refractive astigmatism is the sum of corneal astigmatism and lenticular astigmatism. The real corneal topography technology of the present invention can be either a rasterphotogrammetry technique (PAR Vision System, New Hartford, N.Y.), or a laser holography technique (Eye Technology, Inc., St. Paul, Minn.) or any technique of true corneal topography such as the Orbscan (Orbtek, Lake City, Utah). The techniques of the present invention can enhance uncorrected acuity regardless of pupil size (ambient lighting), reduce spherical aberration, and enhance depth of focus. The technique of using rasterphotogrammetry and the like as an adjunct to other types of ophthalmological surgery is described in my co-pending application entitled "Method of Calibrating Lasers for Use in Ophthalmological Surgery," and having Ser. No. 08/055,578, filed May 3, 1993 the disclosure of which is hereby incorporated by reference.

SUMMARY OF THE INVENTION

It is, therefore, a principal object of the method of present invention to provide surgical correction of astigmatism while sparing a portion of the visual axis and prevent an unwanted coupling effect.

It is another object of the method of present invention to provide surgical correction of astigmatism in which the dioptric correction is limited to a pie shaped section to spare a portion of the visual axis and prevent an unwanted coupling effect.

Another object of the present invention is to provide a method of surgical correction of astigmatism in which the physician treats a pie-shaped section with a gradual reduction in dioptric correction.

A still further object of the method of the present invention to provide a mathematical vector solution for the determination of lenticular astigmatism.

A still further object of the method of the present invention is to provide a mathematical vector solution for the determination of lenticular astigmatism, elimination of all corneal astigmatism, and correction of the spherical refractive error and lenticular astigmatism.

Another object of the invention is to provide the above mathematical vector solution according to the following formula:

$$LA = RA - KA$$

Where LA is the lenticular astigmatism expressed as a vector, RA is the refractive astigmatism expressed as a vector, and KA is the keratometric (cornea!) astigmatism expressed as a vector.

Another object of the present invention is to treat complex refractive error such as compound hyperopic astigmatism and mixed astigmatism by sphericizing the corneal surface wherein the steepest meridian is ablated until a spherical hyperopia is achieved and then the treatment of the hyperopia is done using standard PRK technologies.

Another object of the method of this invention is the use of a novel array of charge coupled devices (CCD) to gather spatially-resolved refractive error data. The data is used to determine the amount of laser treatment at each point on the corneal surface in order to provide a customized aspheric correction.

BRIEF DESCRIPTION OF THE DRAWINGS

Referring to the drawings.

DESCRIPTION OF THE PREFERRED EMBODIMENT

Figure 1:
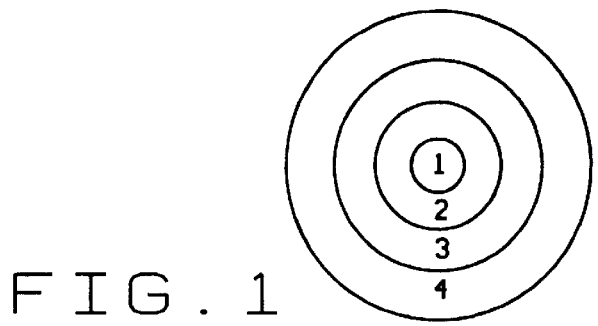
FIG. 1 is a schematic illustrating a refractive map.

One preferred method of treating refractive error of the present invention is illustrated by referring to FIG. 1. The physician first determines point-to-point refractive error, creating a refractive map, as shown in the drawing. The physician then determines the treatment zone subject to laser ablation based upon those determinations. The resultant refractive error map guides the laser connection. For example, in zone (1), the refractive error might be −5 diameters, in zone (2) the refractive error might be −4.25 diameter zone (3) might be −3.87 diameter and zone (4) might be −3.25 diameter.

Figure 4:
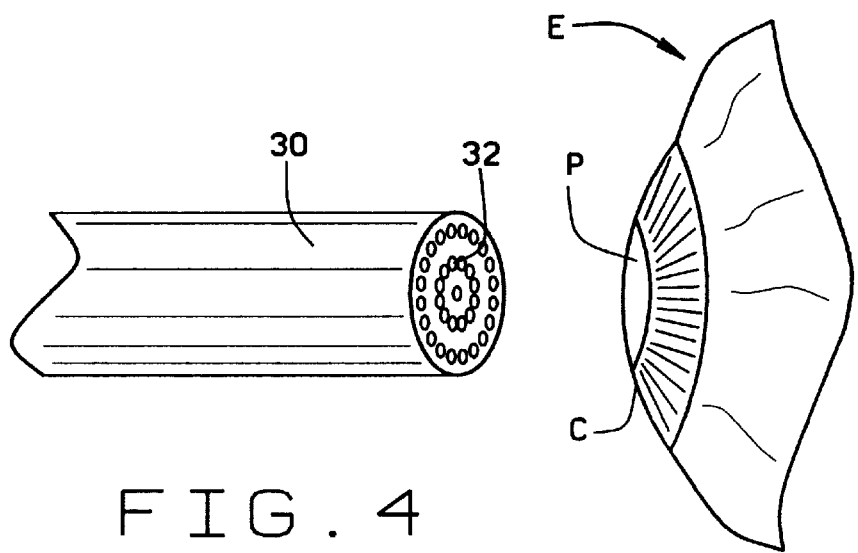
FIG. 4 is a diagram of the charge-coupled device array for spatially-resolved refractions.
Figure 5:
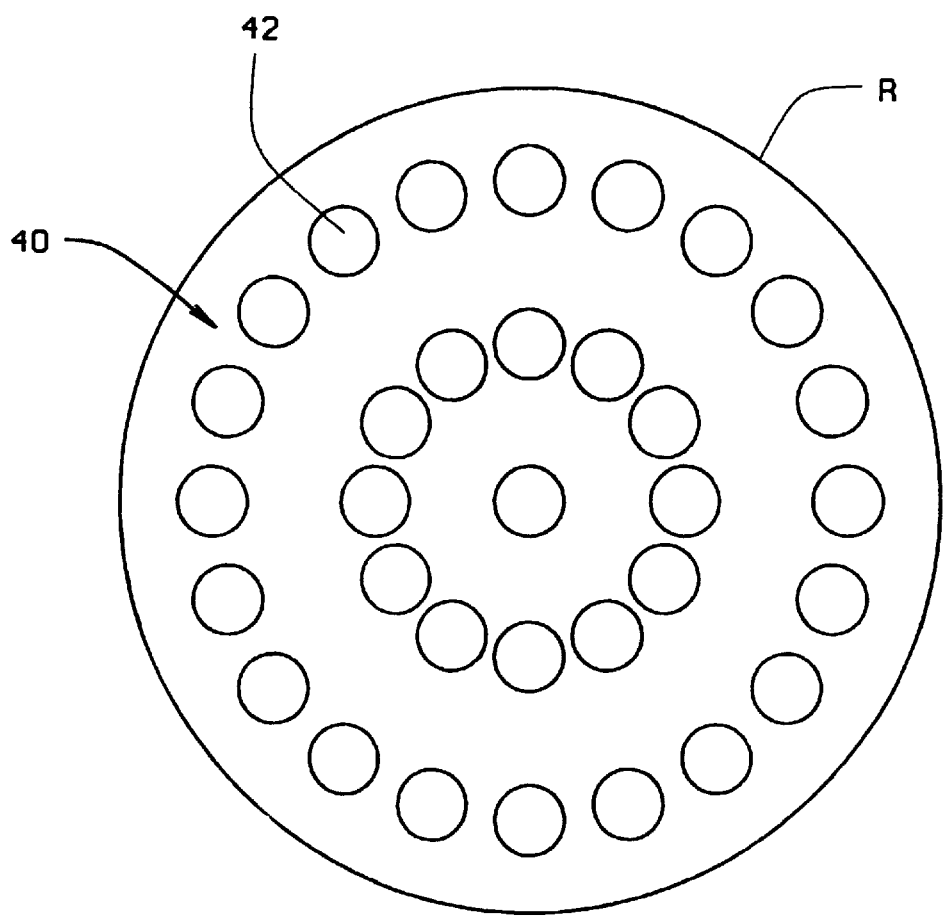
FIG. 5 is a charge coupled array end view.

FIG. 4 illustrates the charge-coupled device for spatially-resolved refractive data. The result is a refractive map showing the local refractive error at each point overlying the entrance pupil while FIG. 5 shows the appearance of the charge-coupled device (CCD) array on the corneal surface. As illustrated in FIGS. 4 and 5, an array of charge coupled devices is used to provide point-to-point information on the refractive error, including any astigmatism, across the pupil, in FIG. 4 probe 30 with CCD projector lens 32 is aimed at corneal surface C at pupil P. FIG. 4 shows an array 40 of CCD's 42 on corneal surface C used to determine the amount of laser treatment required at each point on the corneal surface in order to provide customized aspheric correction.

The present invention uses an array of charge coupled devices (CCD) 42 to provide a spatially-resolved refraction (FIG. 4). Commercially available CCDs as small as 400 microns in diameter (M&M Medical, Tokyo, Japan) are arranged at the center and at evenly spaced intervals along the perimeter of a 35 mm optical zone and concentric perimeter out to an 8 mm optical zone. The microlens assembly 32 for each COD is adjustable. By projecting an in-focus image 40 onto the retina, the localized refractive data is used in order to customize the laser treatment. Thus, an aspheric correction is achieved, including customized correction of astigmatism as described above.

The spatially-resolved refractive data determinations are used on guide laser ablation to perform a full, customized correction of the individual refractive error. The refractive error map information can be used to guide a computer controlled surgical laser such as the Mini-excimer laser manufactured by LaserSight, Orlando, Fla. Such customized procedures enhance uncorrected acuity regardless of pupil size (ambient lighting), reduces spherical aberration, and enhances depth of focus.

Figure 2:
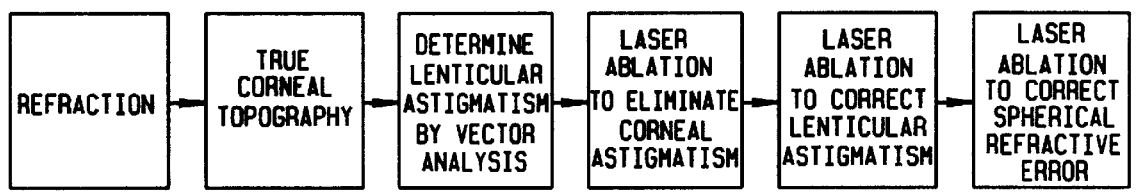
FIG. 2 is a block diagram illustrating one preferred method for treating astigmatism wherein refractive astigmatism is due to corneal and lenticular astigmatism.

In cases where the patient suffers from astigmatism wherein the refractive astigmatism is not the same as the corneal astigmatism, the physician uses a variation of the preferred method, as illustrated in FIG. 2.

FIG. 2 illustrates the sequence of steps taken to identify the presence of lenticular astigmatism, and the treatment of corneal astigmatism before treatment of the lenticular astigmatism. In the first step, as shown in FIG. 2, the physician first determines the refractive astigmatism. Then the true corneal topography is determined. The physician then uses vector mathematics to determine the lenticular astigmatism. A mathematical vector solution determines lenticular astigmatism, eliminates all corneal astigmatism, and allows correction of the spherical refractive error and lenticular astigmatism.

The mathematical vector solution is provided by the following formula:

$$LA=RA-KA$$

Where LA is the lenticular astigmatism expressed as a vector, RA is the refractive astigmatism expressed as a vector, and KA is the keratometric (corneal) astigmatism expressed as a vector.

The corneal astigmatism then is identified by the true corneal topography. A refractive laser such as the Mini-Excimer laser manufactured by LaserSight, Orlando, Fla. is used to eliminate the corneal astigmatism. The physician then uses the laser to treat the lenticular astigmatism and any spherical refractive error as outlined in FIG. 2.

Figure 3:
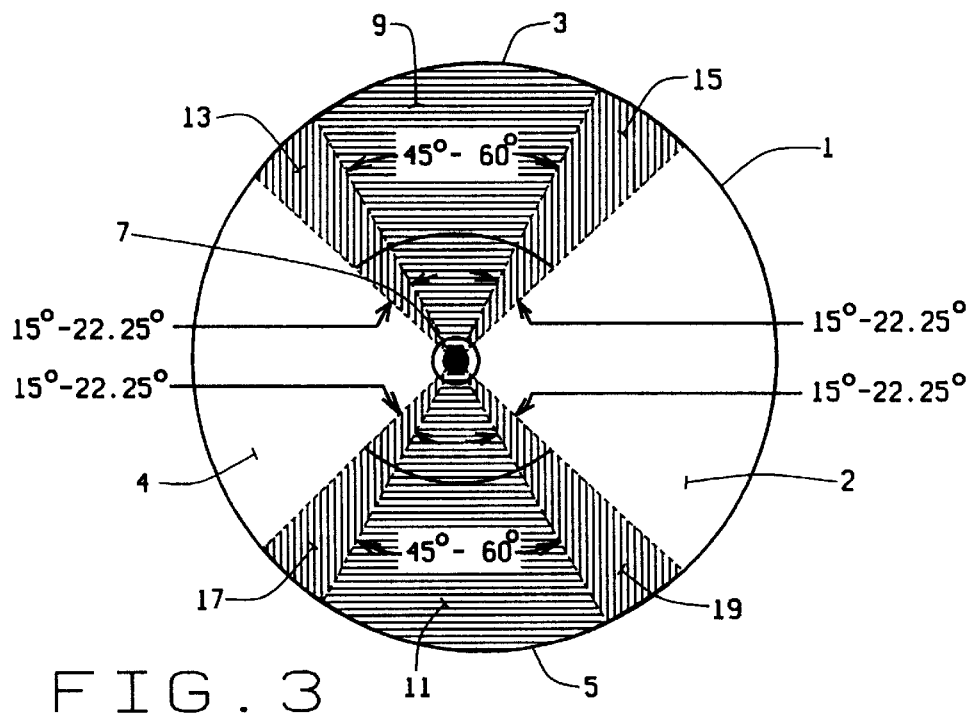
FIG. 3 is a chart disclosing the patterns of ablation used the preferred method for surgical treatment of astigmatism.

FIG. 3 illustrates the pie-shaped sectorial area of astigmatism treatment is a graduated manner wherein the full dioptric connection is limited to the central 45°–60° area (9) and approximately one-half the laser connection is applied to the zone on either side (13 and 15). Note that the visual axis (7) is spared in the unaffected area of cornea (2) and (4). Generally, in the correction of astigmatism, previous art suffers from the lack of predictability and the unwanted coupling effect, that is, unwanted changes in the corneal refractive power in the meridians shown at 2 and 4 of FIG. 3, 90° from the treated meridians. Also, when refractive astigmatism is not the same as corneal astigmatism because of a lenticular astigmatism, an irregular corneal surface (irregular astigmatism) can result. To avoid the unwanted coupling effect, the physician treats a pie-shaped treatment areas 3 and 5 on either side of the visual axis of 7. The full dioptric correction is limited to a 45° to 60° arc, shown as 9 and 11 in each treatment meridian with a gradual or step-wise reduction in dioptric correction, leaving 15° to 22.25° zone of reduced (approximately one-half the dioptric correction) treatment, shown as 13,15 and 17,19. For higher degrees of astigmatism, the arcs encompassing the full correction, 9 and 11, are reduced and the surrounding zones 13, 15 and 17, 19 are increased in size. This gradual reduction in correction of dioptric power in the more peripheral zones 13, 15 and 17, 19 eliminate the unwanted coupling effect in the meridians 2 and which are 90° to the treated meridians. To avoid an irregular corneal astigmatism after treatment, the physician determines the lenticular astigmatism, he then corrects for this astigmatism by treating the cornea after he has eliminated any pre-existing corneal astigmatism.

Variations and modifications in the methods of the present invention may become obvious to those skilled in the art in light of the description and the accompanying illustrations. Therefore, the foregoing description and drawings are to be construed as illustrative and not in a limiting sense.

What is claimed is:

1. A method of performing laser surgery to correct astigmatism without developing an unwanted coupling effect comprising:

determining a point-to-point corneal astigmatic refractive error;

determining a visual axis;

determining a treatment zone adjacent the visual axis based upon the point-to-point corneal astigmatic refractive error and the visual axis;

ablating the treatment zone while sparing said visual axis by ablating the treatment zone in a pie-shaped segment limited to an approximately 45° to approximately 60° arc of the pine-shaped segment on either side of the visual axis; and ablating said treatment zone in a graduated manner.

2. The method of claim 1 wherein the step of ablating said treatment zone in a graduated manner further comprises creating a approximately 15° to approximately 22.25° sector of reduced correction on either side of the full correction treatment zone.

3. The method of claim 1 wherein the step of determining a point-to-point corneal astigmatic refractive error further includes the step of determining the true corneal topography in order to identify the presence of a lenticular astigmatism.

4. The method of claim 3 wherein the step of determining the corneal topography further comprises determining the corneal topography through rasterphotogrammetry.

5. The method of claim 3 wherein the step of determining the corneal topography further comprises of the step of determining the true corneal topography using a variety of nonvideokeratoscopic means.

6. The method of claim 1 wherein said step of sparing the visual axis by ablating said treatment zone in a pie-shaped segment further comprises limiting said full-correction ablation to approximately a 45° to approximately 60° sector in said pie-shaped segment.

7. The method of claim 3 further comprising the step of using vector mathematics to identify the lenticular astigmatic error to guide the laser ablation when the refractive astigmatism is not the same as the corneal astigmatism based upon the formula:

$$LA=RA-KA,$$

wherein LA is the lenticular astigmatism expressed as a vector, RA is the refractive astigmatism expressed as a vector, and KA is a corneal astigmatism expressed as a vector.

8. The method of claim 3 further comprising the step of eliminating any corneal astigmatism prior to a step of correcting for an identified lenticular astigmatism.

* * * * *